(12) United States Patent
Yamamoto (10) Patent No.: US 6,638,274 B2
(45) Date of Patent: Oct. 28, 2003

(54) HIGH-FREQUENCY COAGULATION APPARATUS (75) Inventor: Tetsuya Yamamoto, Hidaka (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/822,589

(22) Filed: Mar. 30, 2001

(65) Prior Publication Data
US 2001/0018587 A1 Aug. 30, 2001

(51) Int. Cl.$^7$ ............................................. A61B 18/14
(52) U.S. Cl. .............................. 606/40; 606/49; 606/50
(58) Field of Search ............................ 606/32, 40, 41, 606/42, 49, 50

(56) References Cited

U.S. PATENT DOCUMENTS

| | | | |
|---|---|---|---|
| 5,256,138 A | | 10/1993 | Burek et al. |
| 5,749,871 A | * | 5/1998 | Hood et al. ................. 606/34 |
| 6,213,999 B1 | * | 4/2001 | Platt et al. ................. 606/34 |
| 6,228,082 B1 | * | 5/2001 | Baker et al. ................ 606/41 |

FOREIGN PATENT DOCUMENTS

| | | | |
|---|---|---|---|
| JP | 9-164149 | * | 6/1997 |
| JP | 10-127658 | * | 5/1998 |

* cited by examiner

Primary Examiner—Lee Cohen
(74) Attorney, Agent, or Firm—Scully, Scott, Murphy & Presser (57) ABSTRACT A high-frequency coagulation apparatus according to the present invention comprises a controller for controlling supply of the fluid from a fluid supply section to a tubular body and controlling supply of the high-frequency electric current from a high-frequency electric current generation section to an electrode, wherein the controller has a first mode for supplying the high-frequency electric current from the high-frequency electric current generation section to the electrode and supplying the fluid from the fluid supply section to the tubular body, and a second mode for supplying the high-frequency electric current from the high-frequency electric current generation section to the electrode and interrupting supply of the fluid from the fluid supply section to the tubular body.

10 Claims, 10 Drawing Sheets

HIGH-FREQUENCY COAGULATION APPARATUS

BACKGROUND OF THE INVENTION

The present invention relates to a high-frequency coagulation apparatus which can be endoscopically used and performs homostasis/coagulation at a part to be treated of a living body such as a bleeding part by causing a high-frequency electric current (coagulation electric current) to flow to the part to be treated.

Jpn. Pat. Appln. KOKAI Publication Nos. 9-164149 and 10-127658, U.S. Pat. No. 5,256,138 and others disclose a high-frequency coagulation apparatus for causing a high-frequency electric current (coagulation electric current) to flow to a bleeding part in order to stop bleeding.

The apparatus disclosed in Jpn. Pat. Appln. KOKAI Publication No. 9-164149 is a monopolar type apparatus comprising gas supplying means for supplying gas capable of being ionized (inert gas such as argon), a high-frequency electric current source (HF source), and one electrode element for leading a coagulation electric current from the HF source into the gas. The gas injected toward a bleeding part by the gas supplying means can be caused to flow to the bleeding part as a coagulation electric current, thereby extensively stopping bleeding at a time.

On the other hand, the apparatus disclosed in Jpn. Pat. Appln. KOKAI Publication No. 10-127658 is a bipolar type apparatus comprising an insertion section main body (probe) having the electrical insulating property, and two electrodes provided to this insertion section main body and is capable of performing homeostasis/coagulation of a tissue positioned between the electrodes by energizing the high-frequency electric current between the two electrodes which come into contact with the tissue.

Further, the apparatus disclosed in U.S. Pat. No. 5,256,138 is an electrosurgical equipment for the surgery and has one hand piece provided with a function being capable of performing dissection or homostasis by using a blade and another function for performing homostasis through conductive gas. In case of an abdominal operation, when a switch provided to the hand piece is used to selectively switch the functions, homostasis utilizing the conductive gas can be performed while effecting dissection.

Meanwhile, although the monopolar type apparatus disclosed in Jpn. Pat. Appln. KOKAI Publication No. 9-164149 is useful for extensive homostasis in particular as an argon beam coagulator (ABC), it is hard to concentrate the coagulation electric current to a desired bleeding part since homostasis is carried out without being in contact with a tissue. Therefore, this apparatus is not suitable for stopping bleeding at a local bleeding part.

On the other hand, although the bipolar type apparatus disclosed in Jpn. Pat. Appln. KOKAI Publication No. 10-127658 is useful for homostasis at a local bleeding part in particular as a bipolar coagulator, the range in which bleeding can be stopped at a time is small since homostasis is carried out while being in contact with the tissue, when extensive homostasis is effected, the probe must be moved across the entire bleeding area, which prolongs the treatment time.

Further, the electrosurgical hand piece disclosed in U.S. Pat. No. 5,256,138 is an apparatus for the abdominal operation, and it can not be hence inserted into a forceps channel in an endoscope for use.

BRIEF SUMMARY OF THE INVENTION

It is an object of the present invention to provide a high-frequency coagulation apparatus which can be endoscopically inserted into a body and which is capable of performing local homostasis/coagulation as well as extensive homostasis/coagulation at a time.

The object of the present invention is achieved by the following high-frequency coagulation apparatus. That is, according to the present invention, there is provided a high-frequency coagulation apparatus comprising: a tubular body having at an end thereof an opening portion which opens in a predetermined direction; a high-frequency electric current generation section for generating a high-frequency electric current; a first electrode exposed and provided at the end portion of the tubular body; a second electrode which performs a coagulation treatment at a part to be treated of a living body positioned between the first electrode and the second electrode in cooperation with the first electrode by causing the high-frequency electric current to flow between the first electrode and the second electrode; energizing means for electrically connecting the first and second electrodes with the high-frequency electric current generation section so as to cause the high-frequency electric current to flow between the first electrode and the second electrode; a fluid supply section for supplying to the tubular body a fluid which is discharged from the opening portion of the tubular body and can transmit the high-frequency electric current supplied to the first electrode to the part to be treated of the living body; and a controller for controlling supply of the fluid from the fluid supply section to the tubular body and controlling supply of the high-frequency electric current from the high-frequency electric current generation section to the electrode, wherein the controller has a first mode for supplying the high-frequency electric current from the high-frequency electric current generation section to the electrode and supplying the fluid from the fluid supply section to the tubular body, and a second mode for supplying the high-frequency electric current from the high-frequency generation section to the electrode and interrupting supply of the fluid from the fluid supply section to the tubular body.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Preferred embodiments according to the present invention will now be described with reference to the accompanying drawings.

Figure 1:
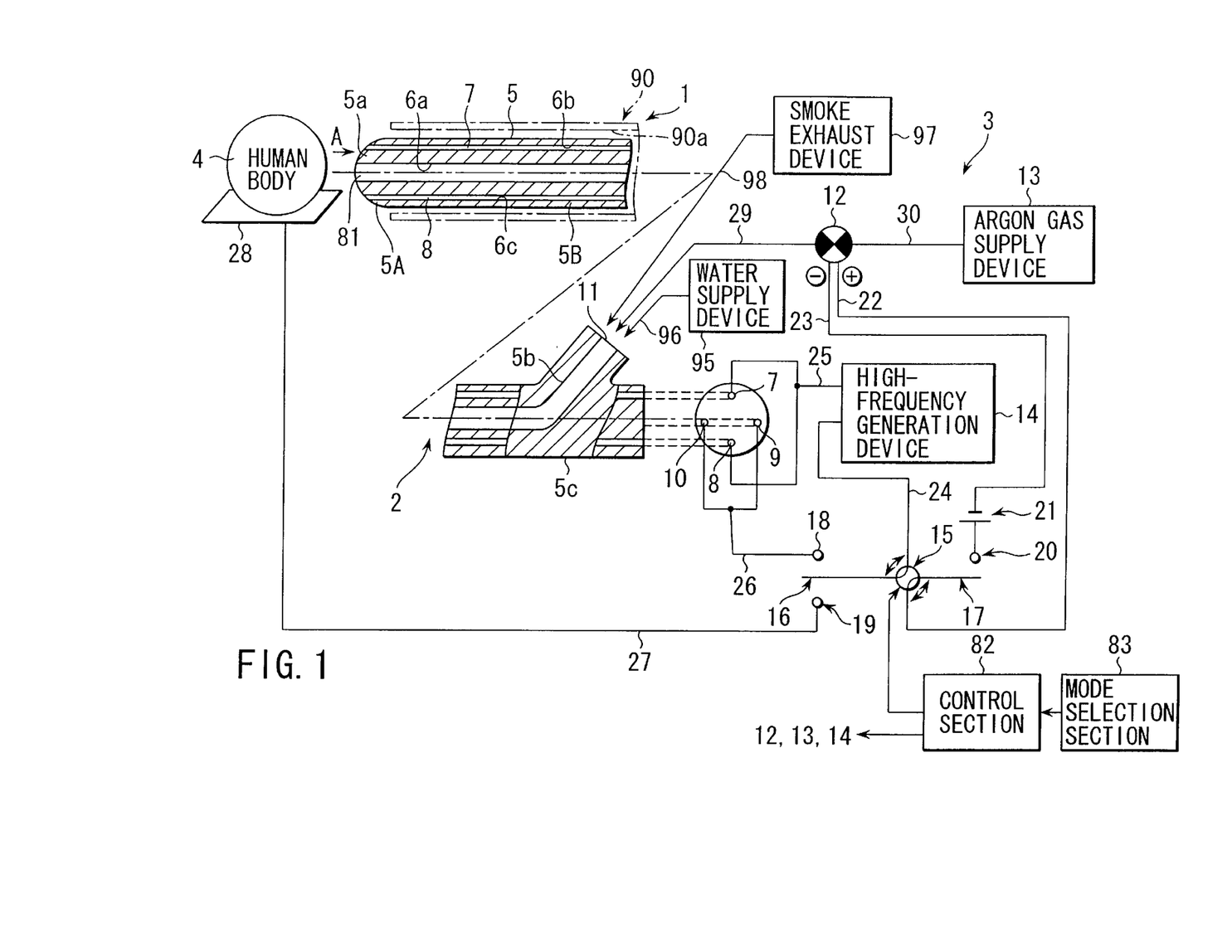
FIG. 1 is a view schematically showing an overall structure of a high-frequency coagulation apparatus according to a first embodiment of the present invention.

FIGS. 1 to 6 show a first embodiment according to the present invention. As shown in FIG. 1, a high-frequency coagulation apparatus 1 of this embodiment is constituted by an insertion section 2 as a tubular body inserted into a body and an operation section (controller) 3 connected to a base end of the insertion section 2.

The insertion section 2 is composed of a catheter (flexible tube) 5 having an elongated multi-lumen structure. The catheter 5 includes: an end portion 5A having a later-described opening portion 81; a base end portion 5C having an opening portion (inlet portion) 11 at which a fluid is led from a later-described argon gas supply device (fluid supply section) 13; and an elongated flexible communication portion 5B which connects the end portion 5A with the base end portion 5C. In this embodiment, the end portion 5A, the base end portion 5C and the communication portion 5B are integrally formed.

Figure 2:
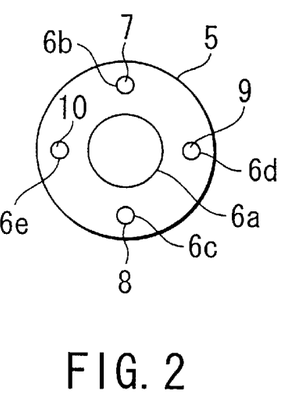
FIG. 2 is a view taken along a direction of an arrow A in FIG. 1.

Further, the catheter 5 has the flexibility and includes five lumens 6a to 6e as shown in FIG. 2 in detail. Furthermore, the catheter 5 has an end surface 5a formed into a semi-spherical shape (semi-spherical shape having a central axis of the catheter 5 at the center thereof, for example) and an external diameter and a length set to dimensions such that the catheter 5 can be inserted into a forceps channel 90a of an endoscope 90. Moreover, the catheter 5 can cause the end portion to which later-described electrodes 7, 8, 9 and 10 and an opening portion 81 are provided to protrude or be retracted from the end opening of the channel 90a of the endoscope 90.

It is to be noted that the insertion section 2 is made of a resin material such as polytetrafluoroethylene (PTFE), tetrafluoroethylene, perfluoro alkoxy ethylene resin (PFA), tetrafluoroethylene hexafluoride propylene resin (FEP), polyolefin, polyamide, vinyl chloride, latex, crude rubber and others. In addition, the end portion of the insertion section 2 is partially made of a heat-resistance material such as polytetrafluoroethylene (PTFE), tetrafluoroethylene, perfluoro alkoxy ethylene resin (PFA), tetrafluoroethylene hexafluoride proplylene resin (FEP), polyolefine, ceramics and others.

As shown in FIG. 2, a central lumen 6a with a large diameter which pierces and extends along the longitudinal direction of the catheter 5 is formed to the shaft center portion of the catheter 5. This central lumen 6a is used as a gas lumen for causing inert gas (argon gas in this embodiment) such as argon or helium to flow, and forms the opening portion 81 at the end portion of the insertion section 2. The opening direction of the opening portion 81 substantially matches with the longitudinal direction of the central axis of the communication section 5B. Additionally, four lumens 6b to 6e each having a small diameter which pierce and extend along the longitudinal direction of the catheter 5 are formed around the gas lumen 6a. In this case, four lumens 6b to 6e are arranged around the central axis of the gas lumen 6a with angular intervals of 90 degrees in the circumferential direction. It is to be noted that the respective lumens 6b to 6e are used as electrode lumens to which high-frequency electrodes 7, 8, 9 and 10 are inserted and arranged.

The respective high-frequency electrodes 7, 8, 9 and 10 are made of metal wires of stainless, aluminium, nickel, brass, titanium, iron, phosphor bronze, tungsten, gold, silver, copper and others or an alloyed metal of these metals. The respective high-frequency electrodes 7, 8, 9 and 10 are fixed in the electrode lumens 6b to 6e by press-fitting or bonding. Further, each of the high-frequency electrodes 7, 8, 9 and 10 may be embedded in the catheter 5 by tubing molding or insert molding. Further, the end surface of each of the high-frequency electrodes 7, 8, 9 and 10 is formed into a semi-spherical shape which is substantially the same as the end surface 5a of the catheter 5 and positioned so as to be flush with or slightly protrude from the end surface 5a of the catheter 5. Moreover, the base end surface of each of the high-frequency electrodes 7, 8, 9 and 10 is exposed at the base end surface of the catheter 5.

It is to be noted that the base end side of the gas lumen 6a extends from the shaft center of the catheter 5 toward the side portion so as not to interfere with the high-frequency electrodes 7, 8, 9 and 10 and is opened at an opening portion 11 of a mouth ring 5b formed so as to protrude toward the side portion of the catheter 5.

On the other hand, the controller 3 includes: an argon gas supply device (fluid supply section) 13 for supplying argon gas as a fluid; a high-frequency generation device (high-frequency electric current generation section) 14 for generating a high-frequency electric current; three electrical contacts 18, 19 and 20; a changeover switch (first control section) 15 for switching the connection state of the electrical contacts 18, 19 and 20; and a control section (third control section) 82 for controlling these operations. In addition, a mode selection section 83 for switching later-described modes is provided to the controller 3 or provided as a separate member.

The argon gas supply device 13 is connected to the opening portion 11 of the mouth ring 5b formed at the base end portion of the insertion section 2 through first and second gas supply pipes 29 and 30. A solenoid valve (second control section) 12 is inserted between the first gas supply pipe 29 and the second gas supply pipe 30. This solenoid valve 12 is of a "normal close" type that the solenoid valve is held at a close position (connection of the ducts 29 and 30 is blocked at this close position) in the non-energization state and controlled by a control section 82.

The high-frequency generation device 14 is electrically connected to the base ends of the high-frequency electrodes 7 and 8, which are exposed at the base end surface of the catheter 5 through an insulating-coated electric wire (energizing means) 25. The first electrical contact 18 is electrically connected to the base ends of the high-frequency electrodes 9 and 10 exposed at the base end surface of the catheter 5. The second electrical contact 19 is connected to a metal P plate (counter electrode plate) 28 through an electric wire (energizing means) 27. The P plate 28 is bonded to a human body 4 by an adhesive tape and the like in such a manner that its metal portion comes into contact with the human body 4. Further, the third electrical contact 20 is connected to a negative side of the solenoid valve 12 through a power supply 21 (energizing means) and an electrical wire (energizing means) 23.

The changeover switch 15 for switching the connection state of the electrical contacts 18, 19 and 20 is constituted as a rotary switch and has a first segment 16 which can come into contact with the first and second electrical contacts 18 and 19 and a second segment 17 which can come into contact with the third electrical contact 20. That is, the changeover switch 15 can rotate between a neutral position (see FIG. 1) at which the first and second segments 16 and 17 do not come into contact with any of the electrical contacts 18, 19 and 20, a first connection position (see FIG. 4) at which the first segment 16 comes into contact with the second electrical contact 19 and the second segment 17 comes into contact with the third electrical contact 20, and a second connection position (see FIG. 6) at which the first segment 16 comes into contact with the first electrical contact 18 and the second segment 17 is held in a state that it does not come into contact with the third electrical contact 20. Further, the first segment 16 is electrically connected to the high-frequency generation device 14 through an electric wire 24. Furthermore, the second segment 17 is connected to a positive polarity side of the solenoid valve 12 through the electric wire 22.

Moreover, a water supply duct 96 connected to a water supply device 95 and a smoke exhaust duct 98 connected to the smoke exhaust device 97 are connected to the base end portion of the catheter 5 so as to communicate with the gas lumen 6a. Therefore, the fluid can be discharged from the end of the catheter 5 through the water supply duct 96 and the gas lumen 6a and the smoke can be sucked from the end of the catheter 5 through the gas lumen 6a and the smoke exhaust duct 98 according to needs. It is needless to say that a separate water supply path or smoke exhaust path (lumen) connected to the water supply duct 96 or the smoke exhaust duct 98 may be formed to the catheter 5 in order to supply the fluid or suck the smoke via the water supply path or the smoke exhaust path.

Description will now be given as to the case where homostasis at a bleeding part is performed by using the high-frequency coagulation apparatus 1 having the above structure.

When performing extensive homostasis/coagulation by using the high-frequency coagulation apparatus 1, the mode selection section 83 (see FIG. 1) is manipulated to set a first mode in the state that the P plate 28 is in contact with the human body 4 and the end of the catheter 5 is opposed to the bleeding part of the human body 4 with a predetermined distance therebetween. When the first mode is set, the control section 82 rotates the changeover switch 15 in the counterclockwise direction from the neutral position shown in FIG. 1 to the first contact position shown in FIG. 4. As a result, the high-frequency coagulation apparatus 1 is set in a non-contact coagulation mode (first mode) in which the first segment 16 comes into contact with the electrical contact 19 and the second segment 17 comes into contact wit the third electrical contact 20 (the high-frequency coagulation apparatus 1 functions as an argon beam coagulator).

Figure 4:
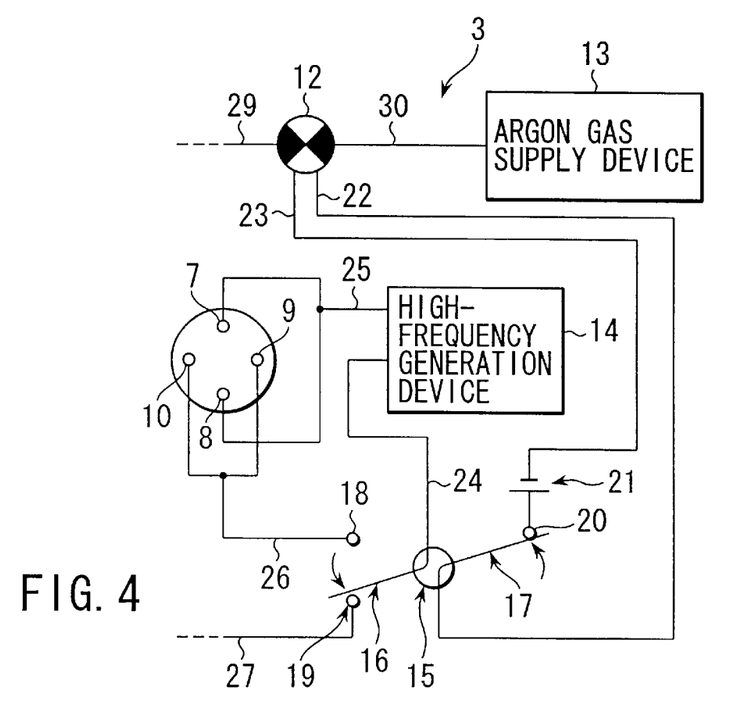
FIG. 4 is a view showing the connection state of a circuit in the non-contact coagulation mode of the apparatus illustrated in FIG. 1.

In this non-contact coagulation mode, the P plate 28 arranged in contact with the human body 4 is connected to the high-frequency generation apparatus 14 through the electric wires 24 and 27 and the segment 16. That is, it is possible to energize the high-frequency electric current from the high-frequency generation device 14 between the high-frequency electrodes (the first electrode) 7 and 8 and the P plate (the second electrode or the third electrode) 28. Further, in this non-contact coagulation mode, the solenoid valve 12 is connected to the power supply 21 through the electric wires 22 and 23 and the segment 17. That is, the electric current flows to the solenoid valve 12 and the solenoid valve 12 is opened. Then, the argon gas from the argon gas supply device 13 can be supplied to the catheter 5 side through the gas supply pipes 29 and 30.

Figure 3:
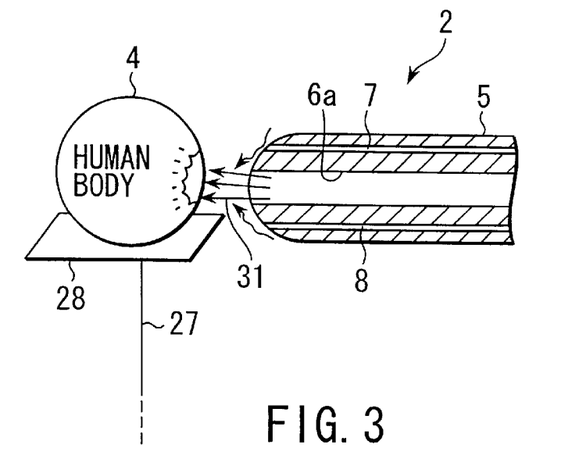
FIG. 3 is a view showing the state of a homostasis treatment performed in a non-contact coagulation mode of the apparatus illustrated in FIG. 1.

Thus, when the argon gas supply device 13 and the high-frequency generation device 14 are operated in the non-contact coagulation mode, the argon gas from the argon gas supply device 13 flows in the gas lumens 6 through the gas supply pipes 29 and 30 and is then injected from the end of the catheter 5 toward the bleeding part of the human body 4, as shown in FIG. 3. Moreover, the high-frequency electric current (coagulation electric current) from the high-frequency generation device 14 flows from the high-frequency electrodes 7 and 8 to the bleeding part of the human body 4 (and to the P plate side) with the argon gas 31 as a medium. That is, the extensive homostasis is enabled at a time.

Figure 5:
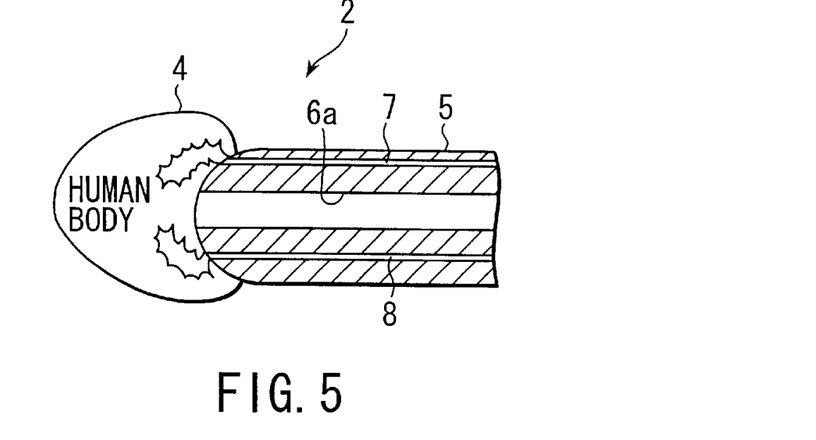
FIG. 5 is a view showing the state of the homostasis treatment performed in a contact coagulation mode of the apparatus illustrated in FIG. 1.

On the other hand, when performing local homostasis/coagulation by using the high-frequency coagulation apparatus 1, the mode selection section 83 (see FIG. 1) is operated to set the second mode in the state that the end of the catheter 5 (to be precise, the electrodes 7, 8, 9 and 10 exposed at the end of the catheter 5) is in contact with the bleeding part of the human body 4 as shown in FIG. 5. When the second mode is set, the control section 82 rotates the changeover switch 15 in the counterclockwise direction from the neutral position shown in FIG. 1 to the second connection position shown in FIG. 6. As a result, the high-frequency coagulation apparatus 1 is set to a contact coagulation mode (second mode) in which the first segment 16 is brought into contact with the first electrical contact 18 and the second segment 17 is held in the non-contact state with the respect to the third electrical contact 20 (the high-frequency coagulation apparatus 1 functions as a bipolar coagulator).

Figure 6:
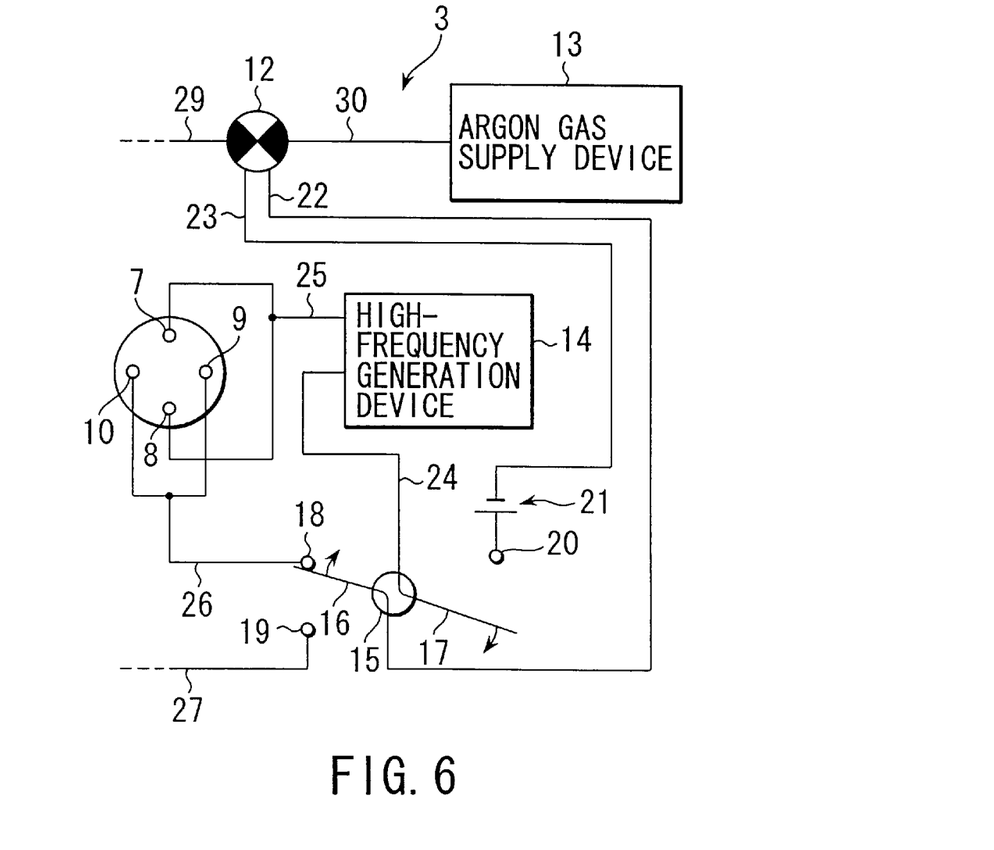
FIG. 6 is a view showing the connection state of the circuit in the contact coagulation mode of the apparatus illustrated in FIG. 1.

In this contact coagulation mode, the high-frequency electrodes 9 and 10 are connected to the high-frequency generation device 14 through the electric wires 24 and 26 and the segment 16. In other words, the high-frequency electric current from the high-frequency generation device 14 can be energized between the high-frequency electrodes 7 and 8 (first electrode) and the high-frequency electrodes 9 and 10 (second electrode). Additionally, in this contact coagulation mode, the electrical connection between the solenoid valve 12 and the power supply 21 is interrupted. That is, the solenoid valve 12 is closed, and the argon gas can not be supplied from the argon gas supply device 13 to the catheter 5 side via the gas supply pipes 29 and 30.

Therefore, in this contact coagulation mode, when the high-frequency generation device 14 is operated, the high-frequency electric current (coagulation electrical current) from the high-frequency generation device 14 flows from the high-frequency electrodes 7, 8 (9, 10) to the high-frequency electrodes 9, 10 (7, 8) through the bleeding part of the human body 4 as shown in FIG. 5. That is, homostasis/coagulation of a tissue which comes into contact with the catheter 5 can be locally effected.

Incidentally, during the homostasis treatment in each mode described above, if the bleeding part is hard to be confirmed, water is supplied to the bleeding part through the water supply duct 96 to temporarily wash the blood. Further, when a field of vision is obstructed by the smoke generated during the high-frequency treatment, the smoke is sucked and emitted to the outside of the body through the smoke exhaust duct 98.

As described above, the high-frequency coagulation apparatus 1 has a non-contact coagulation mode capable of effecting extensive homostasis/coagulation at a time and a contact coagulation mode capable of effecting local homostasis/coagulation. That is, only one high-frequency coagulation apparatus can carry out local homostasis/coagulation as well as extensive homostasis/coagulation at a time. Therefore, it is possible to rapidly cope with various bleeding states and effectively stop bleeding or cauterize a tissue.

Further, since the high-frequency coagulation apparatus 1 of this embodiment can switch each mode by the changeover switch 15, the treatment can be simplified and the treatment time can be shortened.

FIGS. 7 to 13 show a second embodiment according to the present invention. Incidentally, in this embodiment, like reference numerals denote constituent parts equal to those of the first embodiment, thereby omitting the detailed explanation thereof.

Figure 7:
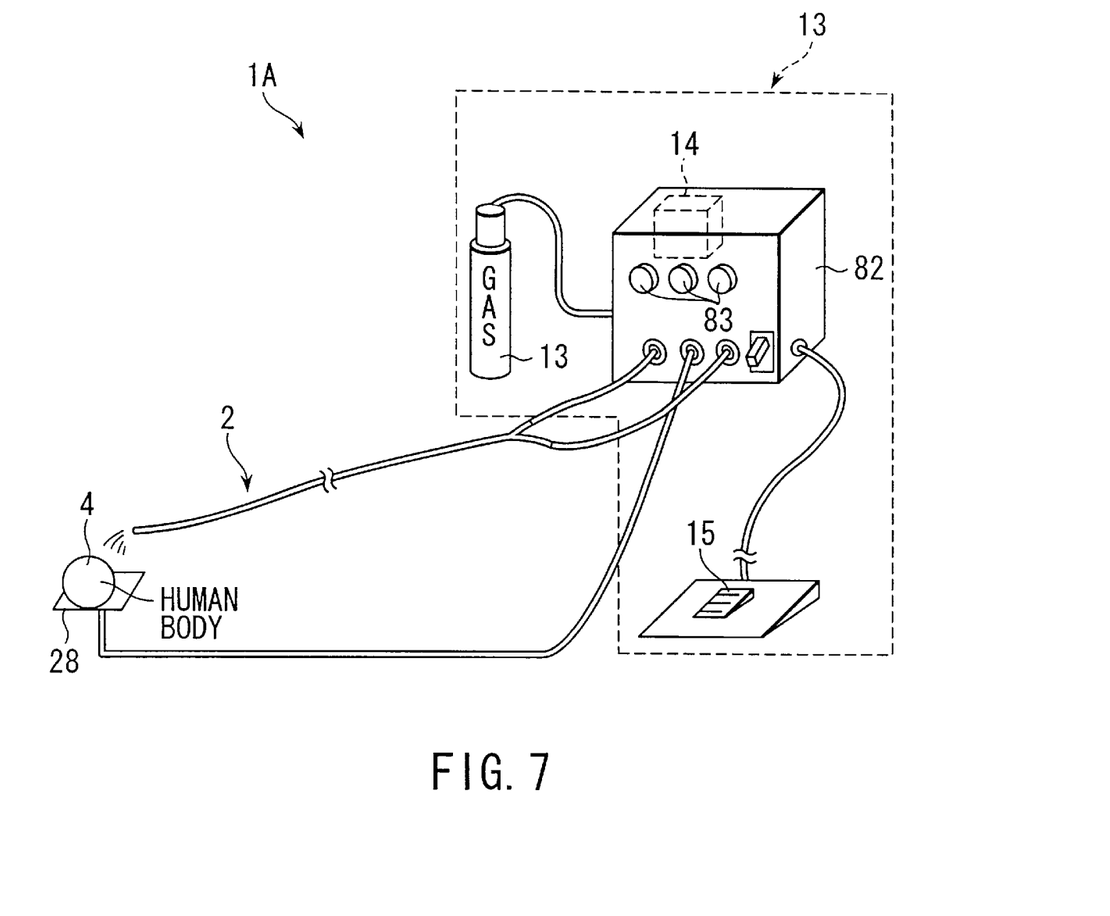
FIG. 7 is a perspective view schematically showing an overall structure of a high-frequency coagulation apparatus according to a second embodiment of the present invention.
Figure 8:
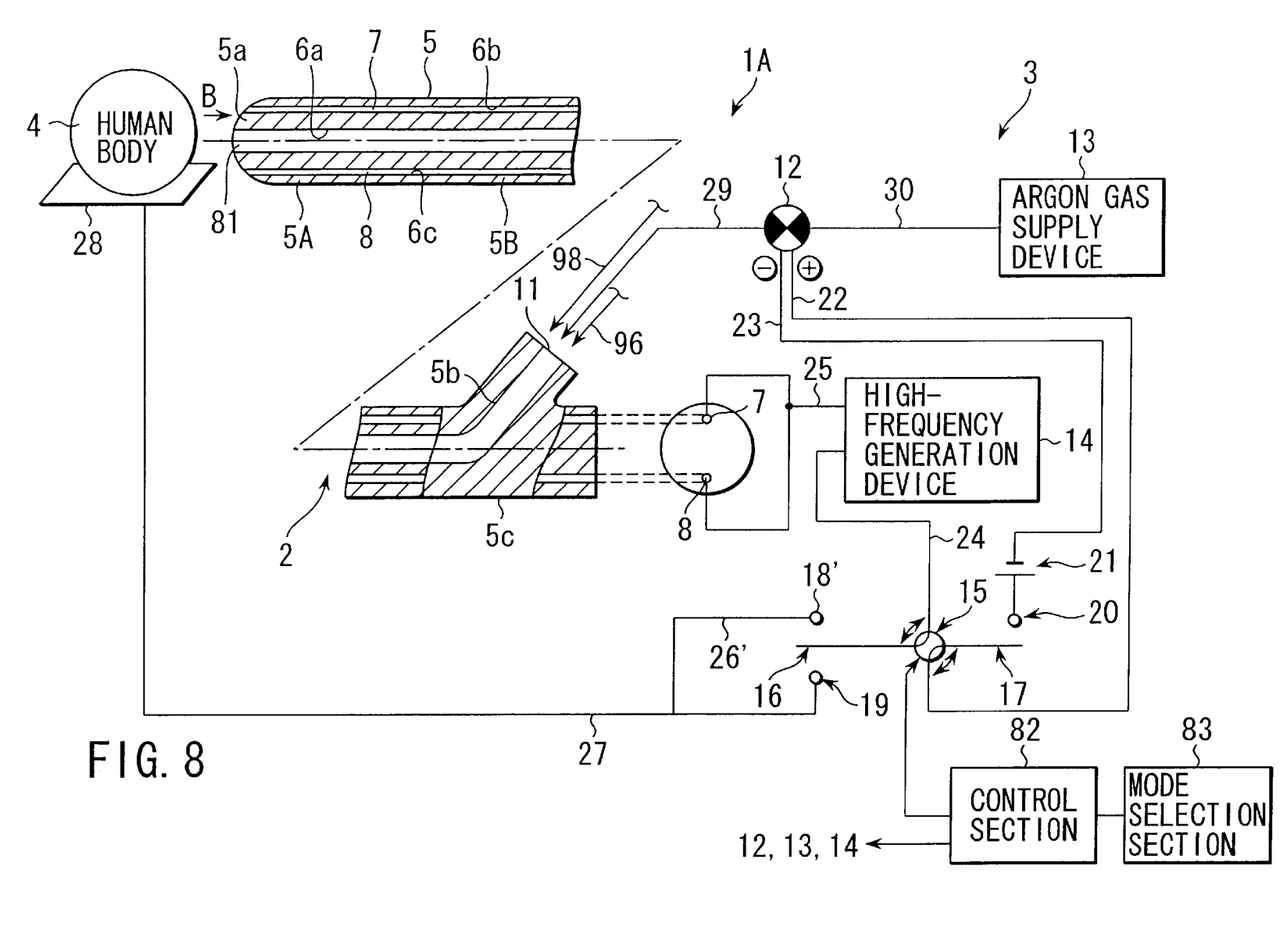
FIG. 8 is a view of an overall structure including a circuit of the high-frequency coagulation apparatus illustrated in FIG. 7.

As shown in FIGS. 7 and 8, a high-frequency coagulation apparatus 1A of this embodiment is constituted by an insertion section 2 inserted into a body and a controller 3 connected to a base end of the insertion section 2.

The insertion section 2 is composed of a catheter 5 having an elongated multi-lumen structure. The catheter 5 is formed of a flexible resin such as PTFE and has three lumens 6a to 6c as shown in FIG. 9 in detail.

Figures 9, 10, 11:
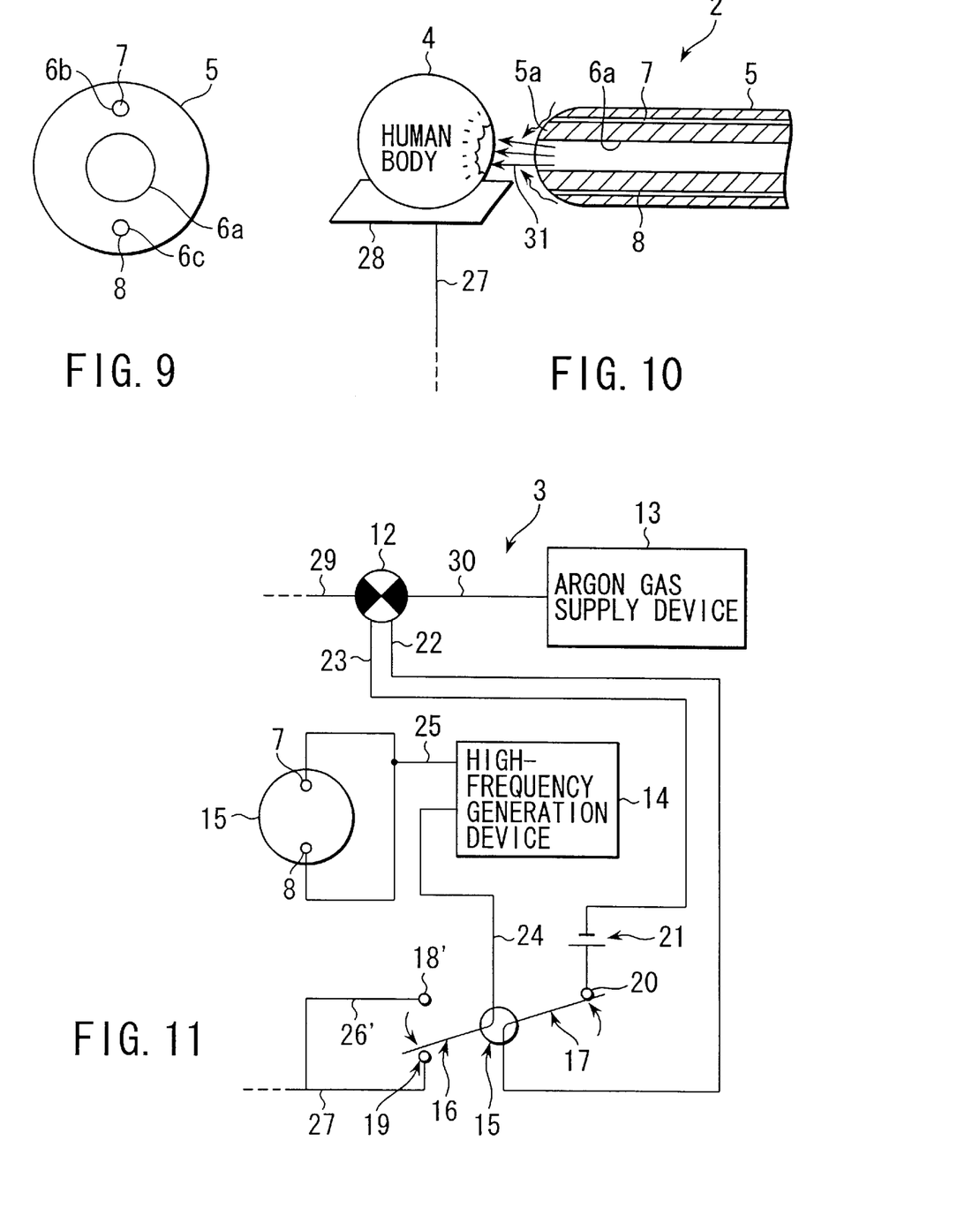
FIG. 9 is a view taken along a direction of an arrow B in FIG. 8.
FIG. 10 is a view showing the state of a homostasis treatment performed in a non-contact coagulation mode of the apparatus illustrated in FIG. 8.
FIG. 11 is a view showing a contact state of a circuit in the non-contact coagulation mode of the apparatus illustrated in FIG. 8.

As shown in FIG. 9, at the shaft center of the catheter 5, the central lumen 6a with a large diameter which is used as a gas lumen for causing inert gas (argon gas in this embodiment) to flow pierces and extends along the longitudinal direction of the catheter 5. Further, the two lumens 6b and 6c each having a small diameter which pierce and extend in the longitudinal direction of the catheter 5 are formed around the gas lumen 6a. In this case, two lumens 6b and 6c are arranged around the central axis of the gas lumen 6a at angular intervals of 180 degrees in the circumferential direction. It is to be noted that the respective lumens 6b and 6c are used as electrode lumens to which the high-frequency electrodes 7 and 8 are inserted and arranged.

The respective high-frequency electrodes 7 and 8 are fixed in the electrode lumens 6b and 6b by press-fitting or bonding. In this case, the end surface of each of the high-frequency electrodes 7 and 8 is formed into a substantially semi-spherical shape which is substantially the same with that of the end surface 5a of the catheter 5 and positioned so as to be flush with or slightly protrude from the end surface 5a of the catheter 5. Further, the base end surface of each of the high-frequency electrodes 7 and 8 is exposed at the base end surface of the catheter 5.

On the other hand, the controller 3 includes: an argon gas supply device 13 for supplying argon gas; a high-frequency generation device 14 for generating a high-frequency electric current; three electrical contacts 18', 19 and 20; and a changeover switch 15 for switching the connection state of these electrical contacts 18', 19 and 20.

The high-frequency generation device 14 is electrically connected through an insulating-coated electric wire 25 to the base ends of the high-frequency electrodes 7 and 8 exposed at the base end surface of the catheter 5. The first electrical contact 18' is connected to an electric wire 27 for connecting the second electrical contact 19 with the metal P plate (counter electrode plate) 28 through an insulating-coated electric wire 26'. Further, the third electrical contact 20 is connected to a negative polarity side of the solenoid valve 12 through the power supply 21 and the electric wire 23.

The changeover switch 15 for switching the connection state of the electrical contacts 18', 19 and 20 is constituted as a rotary switch and has a first segment 16 which can come into contact with the first and second electrical contacts 18' and 19 and a second segment 17 which can come into contact with the third electrical contact 20. That is, the changeover switch 15 can rotate between a neutral position (see FIG. 8) at which the first and second segments 16 and 17 do not come into contact with any of the electrical contacts 18', 19 and 20, a first connection position (see FIG. 11) at which the first segment 16 comes into contact with the second electrical contact 19 and the second segment 17 comes into contact with the third electrical contact 20, and a second connection position (see FIG. 13) at which the first segment 16 is brought into contact with the first electrical contact 18' and the second segment 17 is held in a non-contact state with respect to the third electrical contact 20. In addition, the first segment 16 is electrically connected with the high-frequency generation device 14 through the electric wire 14. Further, the second segment 17 is connected to a positive polarity side of the solenoid valve 12 through the electric wire 22.

Further, a water supply duct 96 and a smoke exhaust duct 98 are connected to the base end portion of the catheter 5 so as to communicate with the gas lumen 6*a*. Therefore, the fluid can be discharged from the end of the catheter 5 through the water supply duct 96 and the gas lumen 6*a* and the smoke can be sucked from the end of the catheter 5 through the gas lumen 6*a* and the smoke exhaust duct 98 according to needs. It is needless to say that a separate water supply path or smoke exhaust path (lumen) connected to the water supply duct 96 or the smoke exhaust duct 98 maybe formed to the catheter 5 without supplying water/emitting smoke through the gas lumen 6*a* so that the fluid can be supplied or the smoke can be sucked through the water supply path or the smoke exhaust path.

Description will now be given as to the case where homostasis is performed at a bleeding part by using the high-frequency coagulation apparatus 1A having the above-described structure.

When performing extensive homostasis/coagulation by using the high frequency coagulation apparatus 1A, the mode selection section 83 (see FIGS. 7 and 8) is operated to set the first mode in the state that the P plate 28 is in contact with the human body 4 and the end of the catheter 5 is opposed to the bleeding part of the human body 4 with a predetermined distance therebetween. When the first mode is set, the control section 82 rotates the changeover switch 15 in the counterclockwise direction from the neutral position shown in FIG. 8 to the first connection position illustrated in FIG. 11. As a result, the high-frequency coagulation apparatus 1A is set in a non-contact coagulation mode in which the first segment 16 is brought into contact with the second electrical contact 19 and the second segment 17 is brought into contact with the third electrical contact 20 (the high-frequency coagulation apparatus 1A functions as an argon beam coagulator).

In the non-contact coagulation mode, the P plate arranged in contact with the human body 4 is connected to the high-frequency generation device 14 through the electric wires 24 and 27 and the segment 16. That is, the high-frequency electric current from the high-frequency generation device 14 can be energized between the high-frequency electrodes (first electrode) 7 and 8 and the P plate (second electrode) 28. Further, in this non-contact coagulation mode, the solenoid valve 12 is connected to the power supply 21 through the electric wires 22 and 23 and the segment 17. In other words, the electric current flows to the solenoid valve 12, and the solenoid valve 12 is opened. Furthermore, the argon gas from the argon gas supply device 13 can be supplied to the catheter 5 side through the gas supply pipes 29 and 30.

Therefore, in this non-contact coagulation mode, when the argon gas supply device 13 and the high-frequency generation device 14 are operated, the argon gas from the argon gas supply device 13 flows into the gas lumens 6 through the gas supply pipes 29 and 30 and is injected from the end of the catheter 5 toward the bleeding part of the human body. Moreover, the high-frequency electric current (coagulation electric current) from the high-frequency generation device 14 flows from the high-frequency electrodes 7 and 8 to the bleeding part of the human body (and to the P plate 28 side) with the argon gas 31 as a medium. That is, extensive homostasis is enabled at a time.

Figure 12:
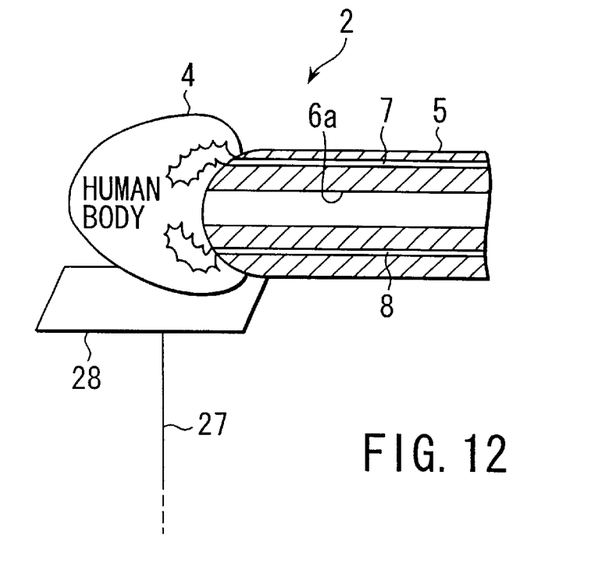
FIG. 12 is a view showing the state of the homostasis treatment performed in a contact coagulation mode of the apparatus illustrated in FIG. 8.

On the other hand, when effecting local homostasis/coagulation by using the high-frequency coagulation device 1A, the mode selection section 83 (see FIGS. 7 and 8) is operated to set the second mode in the state that the end of the catheter 5 (to be precise, the electrodes 7 and 8 exposed at the end of the catheter 5) is in contact with the bleeding part of the human body 4, as shown in FIG. 12. When the second mode is set, the control section 82 rotates the changeover switch 15 in the counterclockwise direction from the neutral position shown in FIG. 8 to the second connection position illustrated in FIG. 13. As a result, the high-frequency coagulation device 1A is set in a contact coagulation mode in which the first segment 16 is brought into contact with the first electrical contact 18' and the second segment 17 is held in a non-contact state with respect to the third electrical contact 20 (the high-frequency coagulation device 1A functions as a monopolar coagulator).

Figure 13:
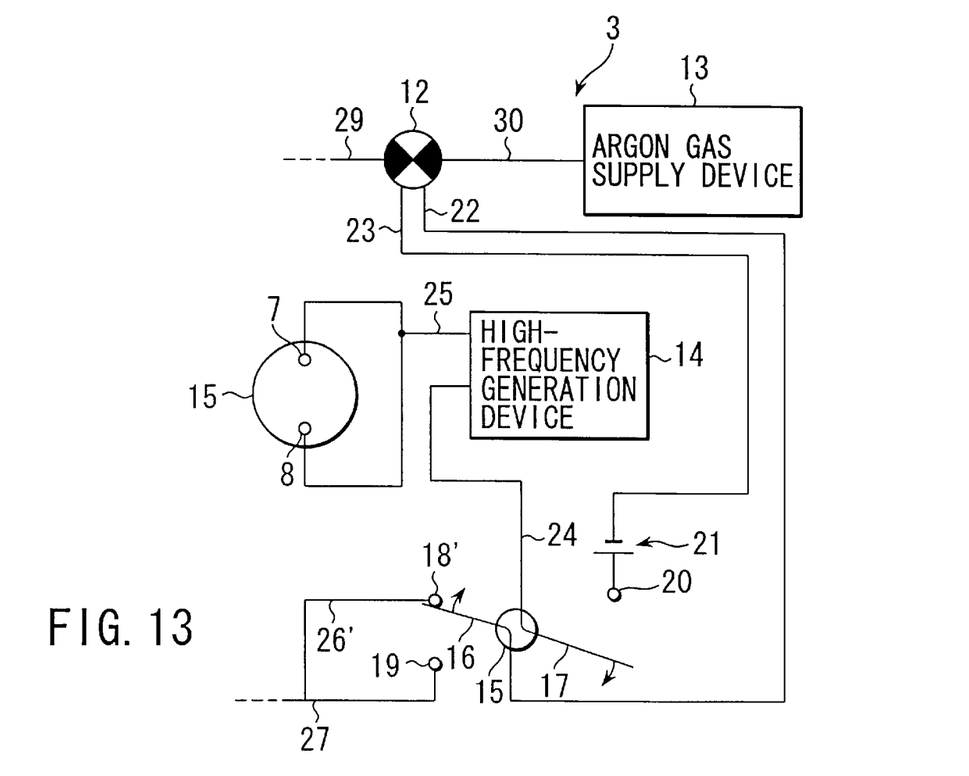
FIG. 13 is a view showing a contact state of a circuit in the contact coagulation mode of the apparatus illustrated in FIG. 8.

In this contact coagulation mode, as similar to the non-contact coagulation mode, the P plate 28 arranged in contact with the human body 4 is connected to the high-frequency generation device 14 through electric wires 24, 27 and 26' and the segments 18'. That is, the high-frequency electric current from the high-frequency generation device 14 can be energized between the high-frequency electrodes (first electrode) 7 and 8 and the P plate (second electrode) 28. Moreover, in this contact coagulation mode, the electrical connection between the solenoid valve 12 and the power supply 21 is interrupted. In other words, the solenoid valve 12 is closed, and the argon gas from the argon gas supply device 13 can not be supplied to the catheter 5 side through the gas supply pipes 29 and 30.

Accordingly, in this contact coagulation mode, when the high-frequency generation device 14 is operated, the high-frequency electric current (coagulation electric current) from the high-frequency generation device 14 flows from the high-frequency electrodes 7 and 8 to the P plate 28 through the bleeding part of the human body 4 as shown in FIG. 12. In other words, homostasis/coagulation of a tissue which comes into contact with the catheter 5 can be locally performed.

Incidentally, during the homostasis treatment in each mode described above, if the bleeding part is hard to be confirmed, water is supplied to the bleeding part through the water supply duct 96 to temporarily wash the blood. In addition, when a field of vision is obstructed by the smoke generated during the high-frequency treatment, the smoke is sucked and emitted to the outside of the body through the smoke exhaust duct 98.

As described above, the high-frequency coagulation device 1A has the non-contact coagulation mode capable of performing extensive homostasis/coagulation at a time and the contact coagulation mode capable of effecting local homostasis/coagulation. That is, only one high-frequency coagulation device 1A can perform local homostasis/coagulation as well as extensive homostasis/coagulation at a time. Therefore, it is possible to rapidly cope with various bleeding states and efficiently stop bleeding or cauterize a tissue.

In addition, since the high-frequency coagulation apparatus 1A of this embodiment can switch each mode by the changeover switch 15, the treatment can be simplified and the treatment time can be shortened.

FIGS. 14 to 20B show a third embodiment according to the present invention. Incidentally, in this embodiment, like reference numerals denote constituent parts equal to those in the first embodiment, thereby omitting the detailed explanation thereof.

Figure 14:
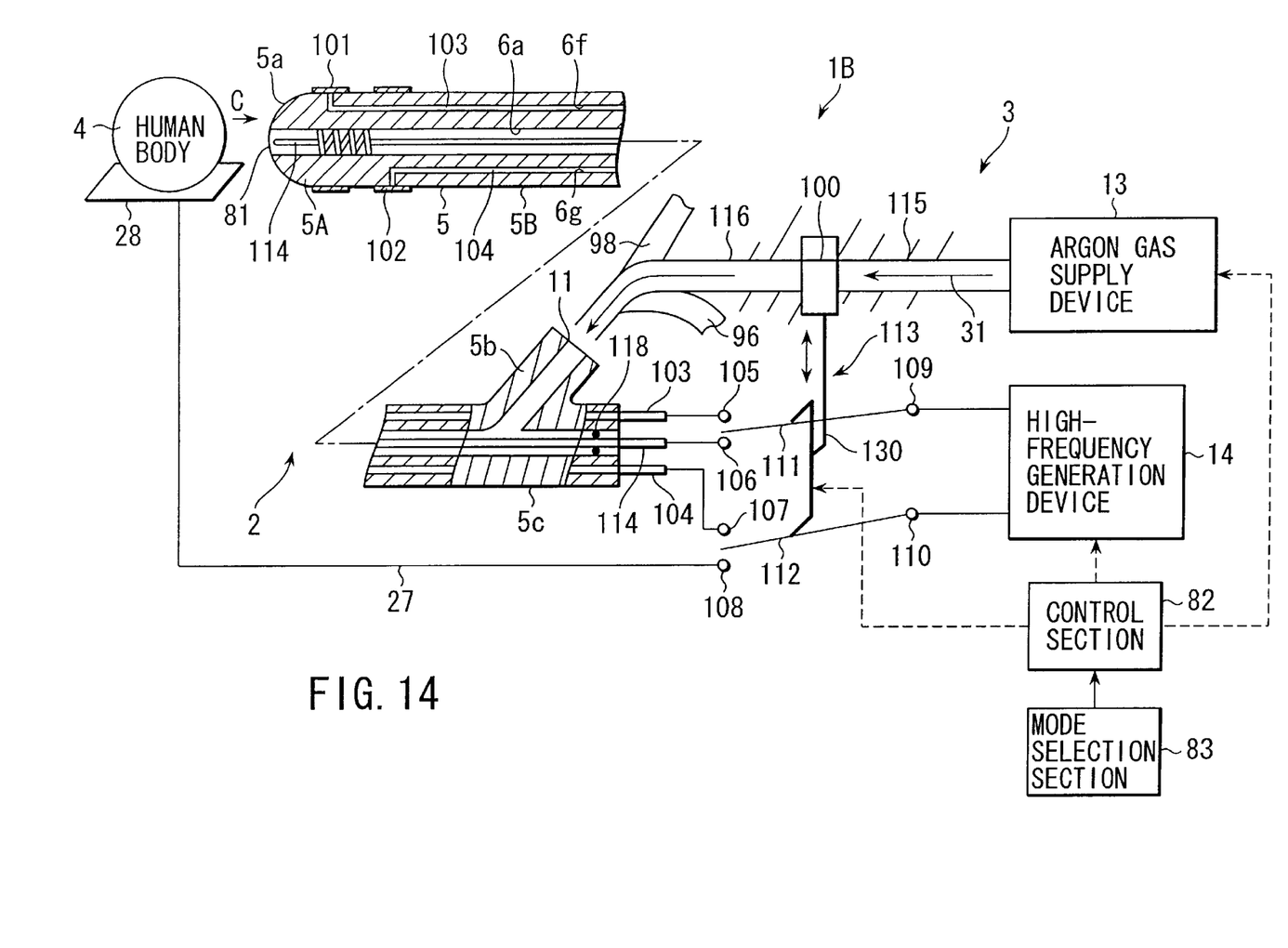
FIG. 14 is a view schematically showing an overall structure of a high-frequency coagulation apparatus according to a third embodiment of the present invention.
Figure 15:
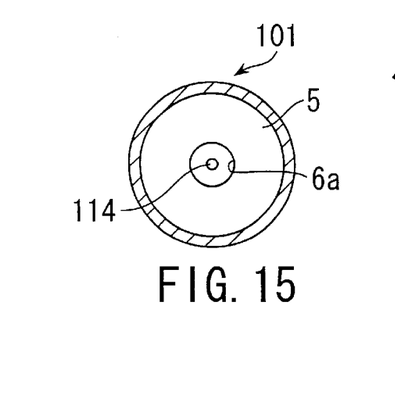
FIG. 15 is a view taken along a direction of an arrow C in FIG. 14.

As shown in FIGS. 14 and 15, a catheter 5 constituting an insertion section 2 of a high-frequency coagulation apparatus 1B according to this embodiment has three lumens 6a, 6f and 6g. Specifically, the central lumen 6a with a large diameter, which pierces and extends along the longitudinal direction of the catheter 5, is formed at the shaft center of the catheter 5. The central lumen 6a is mainly used as a gas lumen for causing inert gas (argon gas in this embodiment) to flow. A high-frequency electrode 114 is inserted into the gas lumen 6a. Since the high-frequency electrode 114 has its end side formed into a spring-like shape to be fixed on the inner surface of the gas lumen 6a, it is positioned at the shaft center of the gas lumen 6a. Further, the end of the high-frequency electrode 114 is arranged at a position where it does not protrude from the end of the catheter 5. Furthermore, the base end side of the high-frequency electrode 114 is fixed to a packing material 118 for preventing gas leakage provided at the base end portion of the gas lumen 6a and arranged in such a manner that the base end side of the high-frequency electrode 114 protrudes from the base end surface of the catheter 5 through the packing material 118 and is exposed.

Moreover, the two lumens 6f and 6g each having a small diameter which extend along the longitudinal direction of the catheter 5 are formed around the gas lumen 6a. In this case, the two lumens 6f and 6g are arranged around the central axis of the gas lumen 6a in the circumferential direction at angular intervals of 180 degrees, and the end side of each of these gas lumens is opened at the side surface of the catheter 5. It is to be noted that these two lumens 6f and 6g are used as electrode lumens into which high-frequency electrodes 103 and 104 are inserted.

Figure 20A:
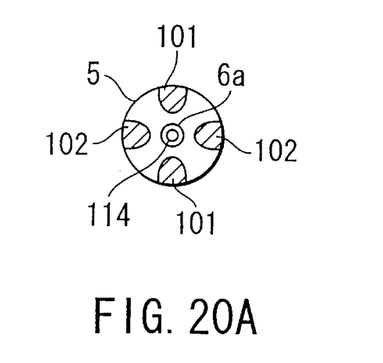
FIG. 20A is a front view showing a modification of the electrode arrangement in the apparatus illustrated in FIG. 14.
Figure 20B:
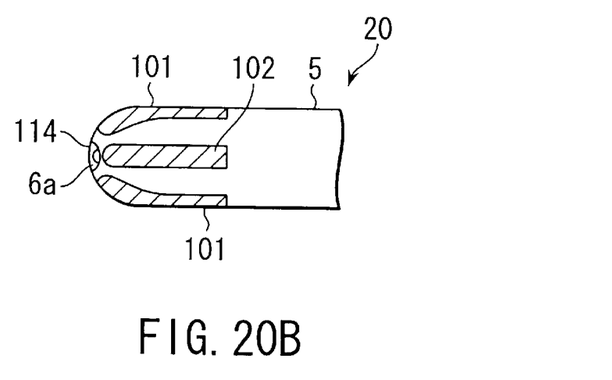
FIG. 20B is a side view showing a modification of the electrode arrangement in the apparatus illustrated in FIG. 14.

The respective high-frequency electrodes 103 and 104 are fixed into the electrode lumens 6f and 6g by press-fitting or bonding. The base end of each of the high-frequency electrodes 103 and 104 protrudes from the base end surface of the catheter 5 and is exposed. In addition, the base ends of the high-frequency electrodes 103 and 104 are respectively connected to cylindrical electrodes 101 and 102 attached on the outer peripheral surface of the catheter 5 on the end side thereof. The cylindrical electrodes 101 and 102 are arranged in such a manner that they are separated from each other by a predetermined distance along the longitudinal direction of the catheter 5, and they are fixed so as to be flush with the outer peripheral surface of the catheter 5 or slightly protrude from the outer peripheral surface of the catheter 5. It is to be noted that the electrodes 101 and 102 are not restricted to the cylindrical shape and may have a belt-like shape which extends along the longitudinal direction of the catheter 5 as shown in FIGS. 20A and 20B, for example. In this case, a plurality of belt-like electrodes 101 and 102 are provided in the circumferential direction of the catheter 5 at equal intervals.

It is to be noted that the base end side of the gas lumen 6a extends from the shaft center of the catheter 5 toward the side portion of the same so as not to interfere with the high-frequency electrodes 101 and 102 and is opened at an opening portion 11 of a mouth ring 5b formed on the side portion of the catheter 5 so as to protrude therefrom, as similar to the first embodiment.

On the other hand, a controller 3 includes: an argon gas supply device 13; a high-frequency generation device 14; four electrical contacts 105, 106, 107 and 108; a changeover switch (first control section) for switching the connection state of these electrical contacts 105, 106, 107 and 108; and a control section (third control section) 82 for controlling these operations. Additionally, a later-described mode selection section 83 for switching modes is provided to the controller 3 or provided separately from the controller 3.

The argon gas supply device 13 is connected to the opening portion 11 of the mouth ring 5b formed at the base end portion of the insertion section 2 through first and second gas supply pipes 115 and 116. A valve (second control section) 100 capable of moving between a close position and an open position is inserted between the first gas supply pipe 115 and the second gas supply pipe 116. This valve 100 is arranged (situated at the close position) so as to interrupt the connection between the ducts 115 and 116 when the changeover switch 113 is placed at a later-described neutral position (see FIG. 14) and a second connection position (see FIG. 19).

The first electrical contact 105 is electrically connected with the base end of the high-frequency electrode 103 exposed on the base end surface of the catheter 5. The second electrical contact 106 is electrically connected to the base end of the high-frequency electrode 114 exposed on the base end surface of the catheter 5. The third electrical contact 107 is electrically connected to the base end of the high-frequency electrode 104 exposed on the base end surface of the catheter 5. The fourth electrical contact 108 is connected to a metal P plate (counter electrode plate) 28 through an electric wire 27. The P plate 28 is bonded to a human body 4 by an adhesive tape and the like in such a manner that the metal portion thereof comes into contact with the human body 4.

A changeover switch 113 for switching the connection state of the electrical contacts 105, 106, 107 and 108 is configured as a sliding type switch. Further, the changeover switch 113 is constituted by a first segment 111 which swivels around the contact 109 and can come into contact with the first and second electrical contacts 105 and 106, a second segment 112 which swivels around the contact 110 and can come into contact with the third and fourth electrical contacts 107 and 108, and a slide operation section 130 having the electrical insulating property which connects the valve 100 with the respective segments 111 and 112 and converts the swiveling operation of the segments 111 and 112 into the opening/closing operation of the valve 100. That is, the changeover switch 113 (slide operation section 130) can slide between a neutral position (see FIG. 14) at which the first and second segments 111 and 112 do not come into contact with any of the electrical contacts 105, 106, 107 and 108, a first connection position (see FIG. 17) at which the first segment 111 comes into contact with the second electrical contact 106 and the second segment 112 comes into contact with the fourth electrical contact 108, and a second connection position (see FIG. 19) at which the first segment 111 comes into contact with the first electrical contact 105 and the second segment 112 comes into contact with the third electrical contact 107. It is to be noted that the first and second segments 111 and 112 are electrically connected to the high-frequency generation device 14 through the contacts 109 and 110. Further, the operation of the slide operation section 130 is controlled by the control section 82.

Moreover, a water supply duct 96 and a smoke exhaust duct 98 are connected to the base end portion of the catheter 5 so as to communicate with the gas lumen 6a. Therefore, the fluid can be discharged from the end of the catheter 5 through the water supply duct 96 and the gas lumen 6a and the smoke can be sucked from the end of the catheter 5 through the gas lumen 6a and the smoke exhaust duct 98 according to needs. It is needless to say that another water supply path or smoke exhaust path (lumen) connected to the water supply duct 96 or the smoke exhaust duct 98 may be formed to the catheter 5 without performing water supply/smoke exhaust through the gas lumen 6a so that the fluid can be supplied or the smoke can be sucked through the water supply path or the smoke exhaust path.

Description will now be given as to the case where homostasis at a bleeding part is performed by using the high-frequency coagulation device 1B having the above-described structure.

Figure 16A:
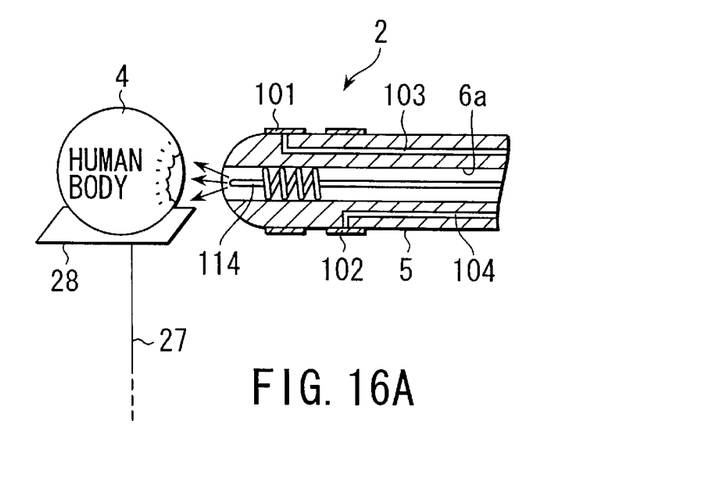
FIGS. 16A and 16B are views showing the state of a homostasis treatment performed in a non-contact coagulation mode of the apparatus illustrated in FIG. 14.
Figure 16B:
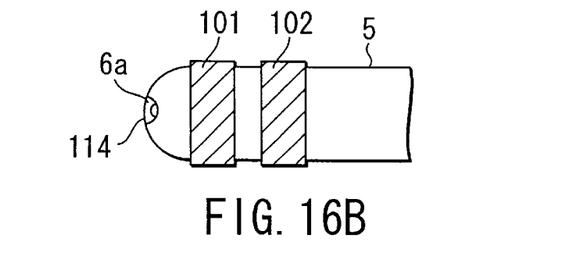

In case of performing extensive homostasis/coagulation by using the high-frequency coagulation device 1B, the mode selection section 83 (see FIG. 14) is operated to set the first mode in the state that the P plate 28 is in contact with the human body 4 and the end of the catheter 5 is opposed to the bleeding part of the human body 4 with a predetermined distance therebetween, as shown in FIGS. 16A and 16B. When the first mode is set, the control section 82 slides the changeover switch 113 downward from the neutral position shown in FIG. 14 to the first connection position shown in FIG. 17. As a result, the high-frequency coagulation device 1B is set in a non-contact coagulation mode in which the first segment 111 comes into contact with the second electrical contact 106 and the second segment 112 comes into contact with the fourth electrical contact 108 (the high-frequency coagulation apparatus 1B functions as an argon beam coagulator).

Figure 17:
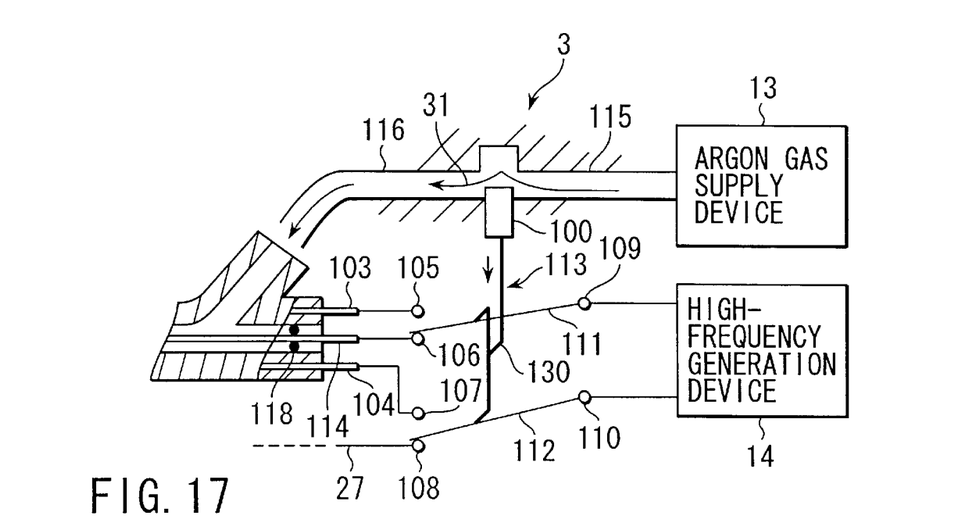
FIG. 17 is a view showing a contact state of a circuit in the non-contact coagulation mode of the apparatus illustrated in FIG. 14.

In the non-contact coagulation mode, the P plate 28 arranged in contact with the human body 4 is connected to the high-frequency generation device 14 through the electric wire 27 and the segment 112, and the high-frequency electrode 114 arranged in the gas lumen 6a is connected to the high-frequency generation device 14 through the segment 111. That is, the high-frequency electric current from the high-frequency generation device 14 can be energized between the high-frequency electrode (the first electrode) 114 and the P plate (the second electrode or the third electrode) 28. Additionally, in this non-contact coagulation mode, the valve 100 is moved from the close position to the open position in synchronization with the swiveling operation of the segments 111 and 112. In other words, the argon gas from the argon gas supply device 13 can be supplied to the catheter 5 side through the gas supply pipes 115 and 116.

Therefore, in this non-contact coagulation mode, when the argon gas supply device 13 and the high-frequency generation device 14 are operated, the argon gas from the argon gas supply device 13 flows into the gas lumens 6 through the gas supply pipes 115 and 116 and is injected toward the bleeding part of the human body 4 from the end of the catheter 5. Further, the high-frequency electric current (coagulation electric current) from the high-frequency generation device 14 flows from the high-frequency electrode 114 to the bleeding part of the human body 4 (and to the P plate 28 side) with the argon gas 31 as a medium. That is, extensive homostasis is enabled at a time.

On the other hand, in case of performing local homostasis/coagulation by using the high-frequency coagulation apparatus 1B, the mode selection section 83 (see FIG. 14) is operated to set the second mode in the state that the end portion of the catheter 5 (to be precise, the cylindrical electrodes 101 and 102) is in contact with the bleeding part of the human body 4. When the second mode is set, the control section 82 slides the changeover switch 113 upwards from the neutral position shown in FIG. 14 to the second connection position shown in FIG. 19. As a result, the high-frequency coagulation apparatus 1B is set in the contact coagulation mode in which the first segment 111 comes into contact with the first electrical contact 105 and the second segment 112 comes into contact with the third electrical contact 107 (the high-frequency coagulation device 1B functions as a bipolar coagulator).

Figure 19:
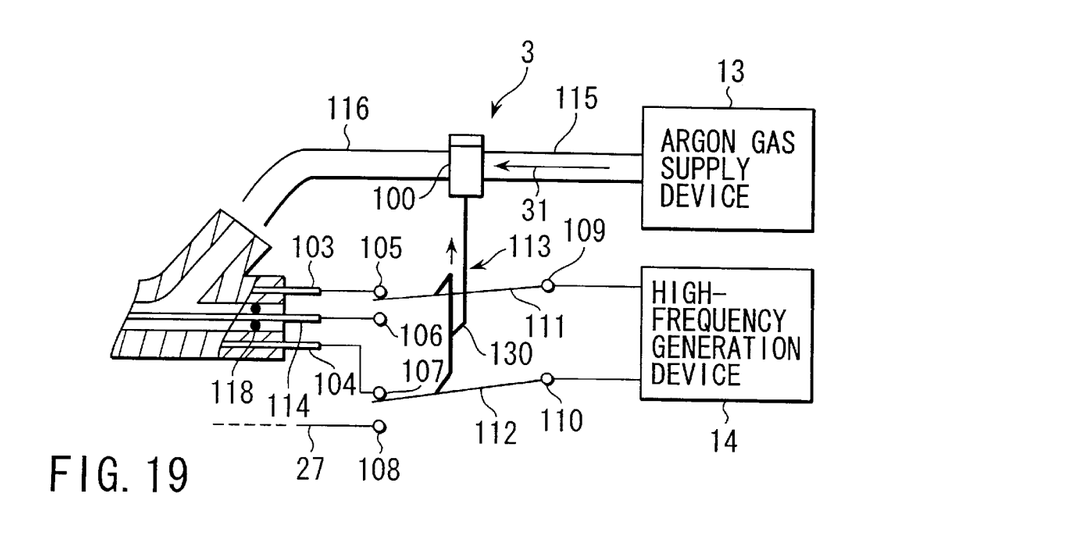
FIG. 19 is a view showing a contact state of a circuit in the contact coagulation mode of the apparatus illustrated in FIG. 14.

In this contact coagulation mode, the high-frequency electrodes (second electrode) 103 and 104 are connected to the high-frequency generation device 14 through the segments 111 and 112. That is, the high-frequency electric current from the high-frequency generation device 14 can be energized between the cylindrical electrode 101 and the cylindrical electrode 102. Moreover, in this non-contact coagulation mode, although the valve 100 is moved in synchronization with the swiveling operation of the segments 111 and 112, the valve 100 maintains the close position at which the connection between the gas supply pipes 115 and 116 is interrupted. That is, the argon gas from the argon gas supply device 13 can not be supplied to the catheter 5 side through the gas supply pipes 115 and 116.

Figure 18:
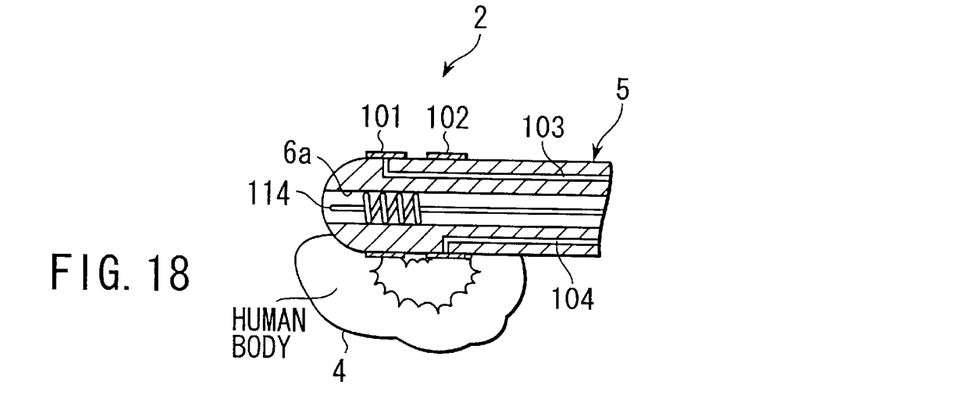
FIG. 18 is a view showing the state of the homostasis treatment performed in a contact coagulation mode of the apparatus illustrated in FIG. 14.

Therefore, when the high-frequency generation device 14 is operated in this contact coagulation mode, the high-frequency electric current (coagulation electric current) from the high-frequency generation device 14 flows from the electrode 101 (102) to the high-frequency electrode 102 (101) through the bleeding part of the human body 4, as shown in FIG. 18. That is, homostasis/coagulation of a tissue which comes into contact with the catheter 5 can be locally performed.

Incidentally, during the homostasis treatment in each mode described above, if the bleeding part is hard to be confirmed, water is supplied to the bleeding part through the water supply duct 96 to temporarily wash the blood. Furthermore, when a field of vision is obstructed by the smoke generated during the high-frequency treatment, the smoke is sucked and emitted to the outside of the body through the smoke exhaust duct 98. In addition, a plurality of electrodes provided to the catheter 5 on the end side thereof may be used in common with both the contact coagulation mode and the non-contact coagulation mode or may be provided separately for each of these modes.

As described above, according to the high-frequency coagulation device 1B of this embodiment, the same results and advantages as those of the first embodiment can be obtained, and the solenoid valve does not have to be used, thereby suppressing the cost as compared with the first embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A high-frequency coagulation apparatus comprising:
   a tubular body having an opening portion which is formed in an end portion of the tubular body, and is open in a predetermined direction;
   a high-frequency electric current generation section for generating a high-frequency electrio current;
   a first electrode provided on the end portion of the tubular body;
   a second electrode capable of performing a coagulation treatment on a part to be treated of a living body which is located between the first and second electrodes, in cooperation with the first electrode, when the high-frequency electric current is made to flow between the first and second electrodes;
   a third electrode provided separate from the tubular body to contact the living body;

energizing means for electrically connecting the first and second electrodes to the high-frequency electric current generation section, to thereby cause the high-frequency electric current to flow between the first and second electrodes;

a fluid supply section for supplying to the tubular body a fluid which is to be discharged from the opening portion of the tubular body, and is capable of transmitting a high-frequency electric current to be made to flow between the first and third electrode; and a controller for controlling supplying of the fluid from the fluid supply section to the tubular body, and also supplying of the high-frequency electric current from the high-frequency electric current generation section to the first to third electrodes, wherein the controller has a first mode for supplying the high-frequency electric current from the high-frequency current electric current generation section to the first electrode, and also the fluid from the fluid supply section to the tubular body, and making the current flow to the third electrode by using the fluid, and a second mode for supplying the high-frequency electric current generated from the high-frequency electric current generation section to the second electrode through the first electrode, and stopping the supplying of the fluid from the fluid supply section to the tubular body.

2. The high-frequency coagulation apparatus according to claim 1, wherein in the second mode, the first and second electrodes are configured to contact with the part of the living body such that the high-frequency electric current flows between the first and second electrodes.

3. The high-frequency coagulation apparatus according to claim 1 which further comprises a mode selecting section for selecting one of the first and second modes, and wherein the controller comprises (i) a first control section for controlling supplying of the high-frequency electric current generated from the high-frequency electric current generation section to the electrodes, (ii) a second control section for controlling the supplying of the fluid from the fluid supply section to the tubular body, and (iii) a third control section for controlling the first and second control sections in accordance with selection by the mode selection section.

4. The high-frequency coagulation apparatus according to claim 3, wherein:

the first control section is a switch for switching a connection state of an electric circuit connecting the high-frequency electric current generation section and the electrodes;

the second control section is an open/close valve provided in a circuit extending from the fluid supply section to the tubular body; and the third control section controls the switch and the open/close valve in response to a signal from the mode selecting.

5. The high-frequency coagulation apparatus according to claim 4, wherein operations of the switch and the open/valve are performed in association with each other.

6. The high-frequency coagulation apparatus according to claim 1, wherein the tubular body is insertable into a channel of an endoscope, and the end portion of the tubular body is projectable from a distal opening of the channel of the endoscope.

7. The high-frequency coagulation apparatus according to claim 1, wherein the tubular body is a bendable tube.

8. The high-frequency coagulation apparatus according to claim 1, wherein the fluid supplied from the fluid supply section is an inert gas.

9. The high-frequency coagulation according to claim 1, wherein at least one of the first and second electrodes is embedded in the tubular body by one of tube-molding, and insert-molding, and being bonded within a lumen provided in the tubular body.

10. The high-frequency coagulation apparatus of claim 1, wherein at least one of the first and second electrodes projects from a surface of the tubular body.

* * * * *